United States Patent [19]

Mehra

[11] Patent Number: 4,740,222
[45] Date of Patent: Apr. 26, 1988

[54] RECOVERY AND PURIFICATION OF HYDROGEN FROM REFINERY AND PETROCHEMICAL OFF-GAS STREAMS

[75] Inventor: Yuy R. Mehra, The Woodlands, Tex.

[73] Assignee: Advanced Extraction Technologies, Inc., Houston, Tex.

[21] Appl. No.: 24,561

[22] Filed: Mar. 11, 1987

Related U.S. Application Data

[63] Continuation-in-part of Ser. No. 854,383, Apr. 21, 1986, which is a continuation-in-part of Ser. No. 828,996, Feb. 13, 1986, Pat. No. 4,696,688, and a continuation-in-part of Ser. No. 828,988, Feb. 13, 1986, Pat. No. 4,680,042, which is a continuation-in-part of Ser. No. 808,463, Dec. 13, 1985, Pat. No. 4,692,179, which is a continuation-in-part of Ser. No. 784,566, Oct. 4, 1985, Pat. No. 4,817,038, which is a continuation-in-part of Ser. No. 759,327, Jul. 26, 1985, Pat. No. 4,623,371, which is a continuation-in-part of Ser. No. 758,351, Jul. 24, 1985, Pat. No. 4,601,738, which is a continuation-in-part of Ser. No. 637,210, Aug. 3, 1984, Pat. No. 4,578,094, which is a continuation-in-part of Ser. No. 532,005, Sep. 14, 1983, Pat. No. 4,526,594, which is a continuation-in-part of Ser. No. 507,564, Jun. 24, 1983, Pat. No. 4,511,381, which is a continuation-in-part of Ser. No. 374,270, May 3, 1982, Pat. No. 4,421,535.

[51] Int. Cl.$^4$ .................................... F25J 3/00
[52] U.S. Cl. ............................ 62/17; 55/69; 62/20
[58] Field of Search ............... 62/9, 11, 16, 17, 20, 62/23, 24, 27–32, 36, 41, 42; 55/68, 69

[56] References Cited

U.S. PATENT DOCUMENTS

| | | | |
|---|---|---|---|
| 1,875,311 | 8/1932 | Voorhees et al. | |
| 2,282,549 | 5/1942 | Sullivan, Jr. et al. | 196/9 |
| 2,573,341 | 10/1951 | Kniel | 260/683 |
| 3,213,151 | 10/1965 | Sherk | 260/667 |
| 3,291,849 | 12/1966 | King et al. | 260/672 |
| 3,349,145 | 10/1967 | Uitti | 260/672 |
| 3,686,344 | 8/1972 | Brunner et al. | 260/679 A |
| 3,877,893 | 4/1975 | Sweny et al. | 55/48 |
| 3,899,312 | 8/1975 | Kruis et al. | 62/17 |
| 4,102,659 | 7/1978 | Martin | 62/17 |
| 4,305,733 | 12/1981 | Scholz et al. | 62/17 X |
| 4,421,535 | 12/1983 | Mehra | 62/17 |
| 4,511,381 | 4/1985 | Mehra | 62/17 |
| 4,552,572 | 11/1985 | Galstraun | 55/36 |
| 4,609,389 | 9/1986 | Karwat | 62/17 |

OTHER PUBLICATIONS

"High $CO_2$–High $H_2S$ Removal with Selexol Solvent", by John Sweny, 59th Annual GPA Convention; Mar. 17–19, 1980, Houston, Texas.

"Gas Absorption", as Chapter 8 in Mass Transfer Operations, by Treybal, McGraw–Hill Book Company, Second Edition, 1986, pp. 221–226 and 393–395.

Primary Examiner—Steven E. Warner
Attorney, Agent, or Firm—Depaoli & O'Brien

[57] ABSTRACT

A hydrogen-containing inlet gas stream is countercurrently extracted with lean solvent to produce an overhead stream of at least 90% purity hydrogen and a bottoms stream of rich solvent which is flashed in one to a plurality of stages. The flashed gas from at least the first stage, after compression, is recycled to the extracting step. The flashed gases from the remaining stages are recovered as fuel gas. When a hydrogen purity of more than 95% is needed, a minor portion of the stripped solvent from the last flashing stage is regenerated in a distillation column to form very lean solvent which is fed to the top of the extractor column while the major portion of the stripped solvent is fed to its middle.

10 Claims, 2 Drawing Sheets

RECOVERY AND PURIFICATION OF HYDROGEN FROM REFINERY AND PETROCHEMICAL OFF-GAS STREAMS

RELATED APPLICATIONS

This is a continuation-in-part of copending application Ser. No. 854,383, filed Apr. 21, 1986, entitled SELECTIVE PROCESSING OF GASES CONTAINING OLEFINS BY THE MEHRA PROCESS, which is a continuation-in-part of co-pending application Ser. No. 828,996, filed Feb. 13, 1986, and now U.S. Pat. No. 4,696,688 continuation-in-part of co-pending application Ser. No. 828,988, filed Feb. 13, 1986, now U.S. Pat. No. 4,680,042 which are continuations-in-part of copending application Ser. No. 808,463, filed Dec. 13, 1985, now U.S. Pat. No. 4,692,179 which is a continuation-in-part of co-pending application Ser. No. 784,566, filed Oct. 4, 1985, now U.S. Pat. No. 4,817,038, which is a continuation-in-part of co-pending application Ser. No. 759,327, filed July 26, 1985, now U.S. Pat. No. 4,623,371, which is a continuation-in-part of co-pending application Ser. No. 758,351, filed July 24, 1985, now U.S. Pat. No. 4,601,738, which is a continuation-in-part of co-pending application Ser. No. 637,210, filed Aug. 3, 1984, now U.S. Pat. No. 4,578,094, which is a continuation-in-part of application Ser. No. 532,005, filed Sept. 14, 1983, now U.S. Pat. No. 4,526,594, which is a continuation-in-part of application Ser. No. 507,564, filed June 24, 1983, now U.S. Pat. No. 4,511,381, which is a continuation-in-part of application Ser. No. 374,270, filed May 3, 1982, now U.S. Pat. No. 4,421,535.

BACKGROUND OF THE INVENTION

1. Field of the Invention

This invention relates to recovery of hydrogen-rich gas streams from hydrogen-containing gas streams and particularly relates to selective recovery of at least 95% purity hydrogen from a wide variety of refinery off-gases by treatment in accordance with the Mehra Process.

2. Review of the Prior Art

As crudes having higher sulfur content and higher carbon-to-hydrogen ratio continue to be processed and as stricter environmental regulations requiring lower sulfur content are passed, the hydrogen demand is expected to grow. Even though a substantial portion of this increased demand will be met by steam reforming of light hydrocarbons and partial oxidation of heavy hydrocarbons, upgrading of existing off-gas streams is a viable alternative.

There are many small to medium size off-gas streams that contain hydrogen and heavier hydrocarbons which are currently being sent to the fuel systems of petroleum refineries. A summary of various hydrogen source streams containing approximate concentrations of hydrogen is shown in Table I. In most of the refinery and petrochemical applications where hydrogen is used as a reactant, the desired makeup hydrogen has a purity of about 95%. In order to prevent the build-up of reaction byproducts, such as methane, a portion of the recycle stream is customarily purged. Even though such a stream is relatively small, its concentration of hydrogen represents a loss which must be offset by additional hydrogen makeup.

TABLE I

| Sources of Hydrogen Off-Gas Streams | | |
|---|---|---|
| Industry | Source | Approximate Hydrogen Concentration |
| Refining | HT Purge | 25–35 |
|  | FCC Gas | 10–15 |
|  | Cascade Reject | 50–60 |
| Methanol | Purge Gas | 70–80 |
| Ethylene | By-product $H_2$ | 60–90 |
|  | Cracked Gas | 10–35 |
| Coke Oven | Product Gas | 0–5 |
| LPG Dehydrogenation | Product Gas | 58 |
| Toluene HDA | $H_2$ Purge | 57 |
| Cyclohexane | $H_2$ Purge | 42 |
| Carbon Black | Product Gas | 7 |
| Formaldehyde | By-product $H_2$ | 18 |
| Ammonia | Purge Gas | 60 |

Several processes have been used and are currently available for upgrading the quality of such off-gas streams. These processes include cryogenic separation, catalytic purification, pressure swing adsorption, membrane separation, and absorption with a selective solvent. Selection of a suitable process depends upon many factors, some of which are the hydrogen product purity that is desired, hydrogen recovery levels, available pressure drop, pretreatment requirements, off-gas composition, impact of reaction products remaining in the hydrogen product, and turn down capability of the selected process.

The bulk of the industrial hydrogen manufactured in the United States uses the process of steam reforming of natural gas according to the equation $CH_4 + 2H_2O \rightarrow CO_2 + 4H_2$. Other processes utilize partial oxidation of resids, coal gasification, and water hydrolysis, but when proceeding from natural gas to liquid hydrocarbons and then to solid feed stocks, the processing difficulties and manufacturing costs increase.

The impurities usually found in raw hydrogen are $CO_2$, $CO$, $O_2$, $N_2$, $H_2O$, $CH_4$, $H_2S$, and higher hydrocarbons. These impurities can be removed by shift catalysis, $H_2S$ and $CO_2$ removal, PSA process, and nitrogen wash. Upgrading of various refinery waste gases is nearly always more economical than hydrogen production by steam reforming. Composition of the raw gas and the amount of impurities that can be tolerated in the product generally determine the selection of the most suitable process for purification.

U.S. Pat. No. 1,875,311 teaches an absorption process for recovering olefins from still gases formed by distillation, cracking, and the like in oil refinery operations and containing an average of about 35% olefins and about 65% saturated hydrocarbons and hydrogen. This process utilizes water-soluble absorbents, such as 95% ethyl alcohol, glycerine, and glycol, as its absorbent medium, based upon ethylene, for example, being about 5.5 to 6 times more soluble in 95% ethyl alcohol than the saturated hydrocarbons.

An absorption process is disclosed in U.S. Pat. No. 3,213,151 for recovering a recycle stream of 50% hydrogen from a gaseous mixture, comprising hydrogen, methane, and normally liquid hydrocarbons, by absorption with pentanes.

A process is disclosed in U.S. Pat. No. 3,291,849 in which toluene, mixed with other alkyl benzenes, is produced as a lean oil which is used in an absorber to purify a make-up hydrogen stream from a catalytic reformer.

A process is disclosed in U.S. Pat. No. 3,349,145 which comprises treatment of an off-gas stream from a catalytic naphtha reformer which contains 50-90 mole % hydrogen, with the remainder being essentially $C_1$–$C_6$ paraffins. The off-gas stream is passed countercurrently to an absorber oil in an absorber-stripper system. The absorber oil consists essentially of a mixture of $C_9+$ aromatic hydrocarbons (trimethylbenzenes, propylbenzenes, cumene, naphthalene, and diphenyl) having an average molecular weight of 125, a gravity of 20° API, and a hydrogen equivalency of 1.5. A reformer off-gas stream of 75 mol % hydrogen purity is exemplarily upgraded to 82.6 mol % hydrogen purity.

Acetylene is described in U.S. Pat. No. 3,686,344 as being washed out of a cracked gas containing 56% hydrogen and 8% acetylene with a physical solvent such as dimethyl formamide, butyro lactone, tetraethyl glycol dimethyl ether, and preferably, N-methyl pyrrolidone.

A process is described in U.S. Pat. No. 3,877,893 for treating a combustible synthesis gas mixture, derived from fossil fuels by carbonization, cracking, partial combustion, or water gas reaction and containing acid gas and hydrogen, by passing a dialkyl ether of a polyethylene glycol solvent in intimate contact therewith through an absorption zone. The gas mixture exemplarily contains 43 mol % hydrogen.

U.S. Pat. No. 4,552,572 relates to purification of raw gases derived from coal by high temperature gasification. Suitable purification solvents must have preferential selectivity for hydrogen sulfide over carbon dioxide. They include methanol, N-methyl pyrrolidone, and dimethyl ether of polyethylene glycol. Commonly, the raw gas intended for synthesis is divided into two parts, one of which is passed through a shift reactor to convert a major portion of its carbon monoxide to hydrogen by the shift reaction: $CO + H_2O \rightarrow CO_2 + H_2$. As the purification treatments remove impurities, including $CO_2$, the shifted gas, which is rich in hydrogen, and the unshifted gas, which is rich in carbon monoxide, may be blended to produce the ratio of hydrogen to carbon monoxide required for a specific synthesis.

Purification of gases may be necessary in addition to blending, however, depending on the ultimate use thereof. For example, for fuel use, an unshifted gas is used in which 90% or more of the sulfur compounds is removed.

For methanol synthesis, shifted and unshifted gases are blended to obtain a ratio of $H_2$ to $CO$ of 2, and the blend is purified by reducing the CO content to about 5 mole % in the feed gas to methanol synthesis.

For hydrogen use, the gas is shifted to the maximum practical extent. Desulfurization is carried to 1 ppm or less, and $CO_2$ is carried to less than 1 mole % before methanation.

For ammonia production, the purification requirements are similar, but a liquid nitrogen wash may be used instead of methanation.

If natural gas is the desired product, the $H_2$-to-$CO$ ratio needed is 3, according to the equation, $CO + 3H_2 \rightarrow CH_4 + H_2O$. However, for methane synthesis, an alternate reaction is $4CO + 2H_2O \rightarrow CH_4 + 3CO_2$. By properly combining these reactions in the presence of a suitable catalyst, methane can be synthesized without a separate shift step.

A new selective solvent process has recently been available for the extraction of hydrocarbon liquids from natural gas streams. This process, known as the Mehra Process, has also been available for processing inert-rich hydrocarbon gases.

The Mehra Process utilizes a preferential physical solvent for the removal and recovery of desirable hydrocarbons from a gas stream. In the presence of a selected preferential physical solvent, the relative volatility behavior of hydrocarbons is enhanced. The selected solvent also has high loading capacity for desirable hydrocarbons. Since the Mehra Process combines solvent selectivity with its hydrocarbon solubility, the selective hydrocarbon removal step in this process is EXTRACTION.

If hydrocarbons heavier than methane, such as ethane, ethylene, propane, propylene, butanes, etc., are present, they can be selectively removed from the gas stream as a combined liquids product. The hydrocarbon component recoveries can be adjusted to any degree varying in the range of 2–98+% for methane, 2–90+% for ethane, and 2–100% for propane and heavier hydrocarbons.

In the Mehra Process, methane is generally considered to be one of the undesirable hydrocarbons which leaves the process as residual gas. However, as taught in U.S. Pat. No. 4,526,594, the residue gas can be selectively purified to become the product gas. The Mehra Process accordingly provides flexible recovery to a selected degree of only economically desirable hydrocarbons as a hydrocarbon liquids product or as a product gas.

A wide variety of gaseous streams are to be found in petroleum refineries. Some streams are integral parts of a specific process, e.g., they are recycled from a fractionating column to a reactor. Such a recycle stream may be an impure hydrogen stream which must be purified before returning to the reactor and/or combining with a make-up hydrogen stream. Other such gaseous streams may be a byproduct of a major refinery process and may be sent to one or more other processes which are nearby and require a hydrogen feed stream. Purification of these byproduct streams is generally also needed. For example, the byproduct hydrogen stream from an ethylene cracking plant may have a hydrogen content of 75 mol % and may be initially needed as feed to a hydrodealkylation process requiring 95 mol % hydrogen. Or a change in process conditions at a nearby hydroforming plant may create a demand for 99 mol % hydrogen and consequent purification of a 90% hydrogen byproduct stream, for example, that happens to be available.

There is clearly a need in such circumstances to be able to change selectively from one hydrogen purity to another without having to change equipment specifications.

SUMMARY OF THE INVENTION

It is accordingly an object of this invention to provide a process for separating a hydrogen-rich stream and a methane-rich stream from a hydrogen-containing refinery gas stream or a petrochemical off-gas stream.

It is also an object to provide a process for selectively separating hydrocarbons heavier than methane as a hydrocarbon liquids product while separating methane from hydrogen for additionally providing two gaseous products.

In accordance with these objectives and the principles of this invention, a process is herein provided for selectively purifying hydrogen-containing refinery gas streams to a selected degree from 90% to 99% hydrogen purity. This process is an extractive flashing process utilizing a preferential physical solvent in which hydrocarbons are more soluble and less volatile than hydrogen.

Under the normal operating conditions of hydrocarbon distillation systems, the alpha or relative volatility for methane over ethylene is about 5.0. However, as presented at the 59th Annual Gas Processors Association Convention, Mar. 17-19, 1980, in a paper entitled "High $CO_2$-High $H_2S$ Removal with SELEXOL Solvent" by John Sweny, the relative volatility of methane over ethylene is 7.3 at 1000 psia and 77° F. Thus, in the presence of dimethyl ether of polyethylene glycol (DMPEG), which is a preferential physical solvent, the relative volatility of methane over ethylene is considerably improved (46%) when compared to a normal fractionation system, thereby suggesting that DMPEG is selective towards the recovery of ethylene from a stream containing methane and ethylene. Since the relative behavior of methane and ethylene is altered by the presence of a preferential physical solvent such as DMPEG, the process of contact between the gas stream and the physical solvent is selective absorption or better defined as extraction instead of absorption.

The table in the Sweny article, as its FIG. 2, presents the solubilities of various materials from hydrogen to HCN, having R values respectively varying from 0.2 to 18,000, relative to the assumed K value for methane of 1.0. All of the materials more soluble than methane (herein designated "M") can be lumped together as "more soluble than methane" (MSM), and hydrogen and carbon monoxide can be described as "less soluble than methane" (LSM).

If the only LSM material is hydrogen, the process of this invention can be characterized as providing selective capability for recovery according to a selected degree of a hydrogen-rich product stream ranging from 90% hydrogen purity to 99% hydrogen purity, while additionally producing a fuel gas product (M+MSM) from which, if desired, a hydrocarbon liquids product can be recovered as disclosed in U.S. Pat. Nos. 4,511,381, 4,526,594, 4,578,094, and 4,623,371, all of which are incorporated herein by reference.

The process of this invention produces, to a selected degree, a hydrogen-rich gas product stream as an overhead stream and a rich solvent stream as a bottoms stream from an inlet stream of gas comprising hydrogen and hydrocarbons by contacting the inlet hydrogen-containing gas stream with a stream of lean preferential physical solvent in which the hydrocarbons are more soluble and less volatile than hydrogen. The contacting is conducted within at least one column to which the inlet gas stream and the lean solvent stream are fed and within which they pass in countercurrent contact.

The preferential physical solvents are defined for the purposes of this invention as being selective for methane and heavier hydrocarbon components of the gas stream over hydrogen such that: (1) the minimum relative volatility of hydrogen over methane of at least 4.5 (thereby defining its improved selectivity toward methane over hydrogen) and in addition the solubility of methane in the solvent is at least 1.0 standard cubic foot of methane per gallon of the solvent (SCF/GAL) (thereby defining its hydrocarbon loading capacity), or, (2) alternatively, the preferential factor, determined by multiplying the relative volatility of hydrogen over methane by the solubility of methane in solvent, in standard cubic feet (SCF) of methane per gallon of solvent, is at least 4.5. However, the ideal preferential physical solvent has a volatility toward methane over hydrogen of at least 5.5 and would simultaneously possess a hydrocarbon loading capacity of at least 3.5 SCF/GAL or a preferential factor of at least 19.25. When a hydrogen purity of at least 90 mol % and hydrogen recovery of at least 90% are required, a preferential factor of at least 25 is preferred. For obtaining a hydrogen purity of at least 95 mol % and a hydrogen recovery of at least 95%, a preferential factor of at least 39 is highly preferred. All of the above data are defined at 1,000 psig and 77° F.

Additionally, the preferential physical solvent is selected from the group consisting of dialkyl ethers of polyalkylene glycol, N-methyl pyrrollidone, dimethylformamide, propylene carbonate, sulfolane, glycol triacetate, and $C_8$ to $C_{10}$ aromatic compounds having methyl, ethyl, propyl, or butyl aliphatic groups specifically constituting a sub-group of mesitylene, n-propyl benzene, n-butyl benzene, o-xylene, m-xylene, p-xylene, and mixtures thereof and aromatic streams rich in mixed xylenes and other $C_8$-$C_{10}$ aromatics.

The inlet gas stream is selected from the group consisting of thermally cracked hydrocarbon gas, catalytically cracked hydrocarbon gas, refinery off-gas, coke-oven gas, synthesis gas, refinery HT purge gas, refinery FCC gas, refinery cascade reject gas, methanol purge gas, ethylene byproduct hydrogen, ethylene cracked gas, LPG dehydrogenation product gas, toluene HDA hydrogen purge gas, cyclohexane hydrogen purge gas, carbon black product gas, formaldehyde byproduct hydrogen, and ammonia purge gas. In many gas streams, the hydrocarbons principally comprise methane. In other gas streams, the hydrocarbons additionally comprise substantial quantities of olefins and hydrocarbons heavier than methane. The hydrocarbons heavier than methane may comprise ethane, propane, and/or butane, and the olefins may comprise ethylene, propylene, butene, and diolefins.

The solvent selectively extracts the hydrocarbons from the inlet gas stream to provide selective capability for recovery of:

A. a hydrogen gas product stream having a purity of 90% to 99% as the overhead stream; and B. most of the methane and substantially all of the materials more soluble than the methane that are in the solvent, as the fuel gas product stream.

When the process produces relatively pure hydrogen product (>95% hydrogen purity), a regeneration step, within a distillation column, is needed for a slipstream of the solvent. This slipstream is a minor portion of the stripped solvent from the last flashing stage and need never be greater than 40% of the stripped solvent stream.

The regenerated lean solvent stream (herein described as very lean solvent) is cooled and fed to the top of the extraction column, but the flashed solvent stream from the last flashing stage (herein described as lean solvent) is cooled and fed to the approximate middle of the extraction column, so that there are at least two extraction stages within the extraction column to remove substantially all of the methane and substantially all of materials in the gas stream which are more soluble than the methane in the solvent, whereby the overhead stream from the extracting is at least 95% hydrogen. The inlet gas stream is extracted in the first stage of the two stages with a major part of the solvent stream containing less than 10 wgt. % of hydrocarbons to produce a partially stripped gas stream which flows upwardly within the column to enter the second stage created by countercurrent contact with the very lean solvent.

The degree of hydrogen purity and recovery thereof can be partially selected by the size of the slipstream. Additional selectivity can be obtained by selectively controlling the temperatures to which both the major and minor solvent streams are cooled.

The bottoms stream is successively flashed at least twice to produce a fuel gas product stream comprising at least most of the hydrocarbons, and a lean solvent stream which is recycled to the extraction column or columns. When the overhead stream from at least the first of the successive flashing stages is recycled to the column, the overhead streams from the remaining flashing stages are combined to form the fuel gas product stream.

The invention may also be described as a process for separating hydrogen and $C_1+$ hydrocarbons from a hydrogen-containing inlet gas stream, which comprises more than 5 mol % of hydrogen, to produce a hydrogen gas product stream of at least 90 mol % hydrogen purity. This process comprises the following steps:
A. extracting the inlet gas stream with a preferential physical solvent to produce an overhead stream which is at least hydrogen-rich and a bottoms stream which is hydrocarbon-rich solvent;
B. flashing the bottoms stream at a flashing pressure which is selected to be between 800 psia and 2 psia and is sufficiently low that substantially all the $C_1+$ hydrocarbons are separated from a stripped solvent stream and are produced as a stream of flashed-off gases; and
C. recycling the stripped solvent stream to the extracting of Step A.

When the flashing step utilizes up to eight flashing stages, the a ratio of absolute pressures between successive flashing stages is at least 2.0.

If the inlet gas stream is extracted in two stages with lean solvent and then with very lean solvent to remove substantially all of the methane and substantially all of the materials in the gas stream which are more soluble than methane in the solvent, the overhead stream from the extracting is at least 95% hydrogen purity.

Preferably, the inlet gas stream is extracted in the first stage of these two stages with a major part of the solvent stream containing less than 10 wgt. % of hydrocarbons to produce a partially stripped gas stream. Then the partially stripped gas stream is extracted in the second stage of the two stages with a very lean solvent stream to produce the pure hydrogen stream and an enriched solvent stream. Then the enriched solvent stream is thereby added to the major solvent stream in the first stage of these two stages for extracting the inlet gas stream, whereby the rich solvent stream is produced.

Because of the flexibility of component recoveries offered by this technology, the modes of operation are referred to by the lightest component that is extracted. For example, in the recovery and purification of nitrogen from a gas stream as taught in U.S. Pat. No. 4,623,371, if methane is the lightest extracted component, the operation mode would be "methane extraction". If it is additionally desirable to extract ethane and heavier components from the methane, then the process step will be referred to as "ethane extraction".

DESCRIPTION OF THE PREFERRED EMBODIMENTS

Figure 1:
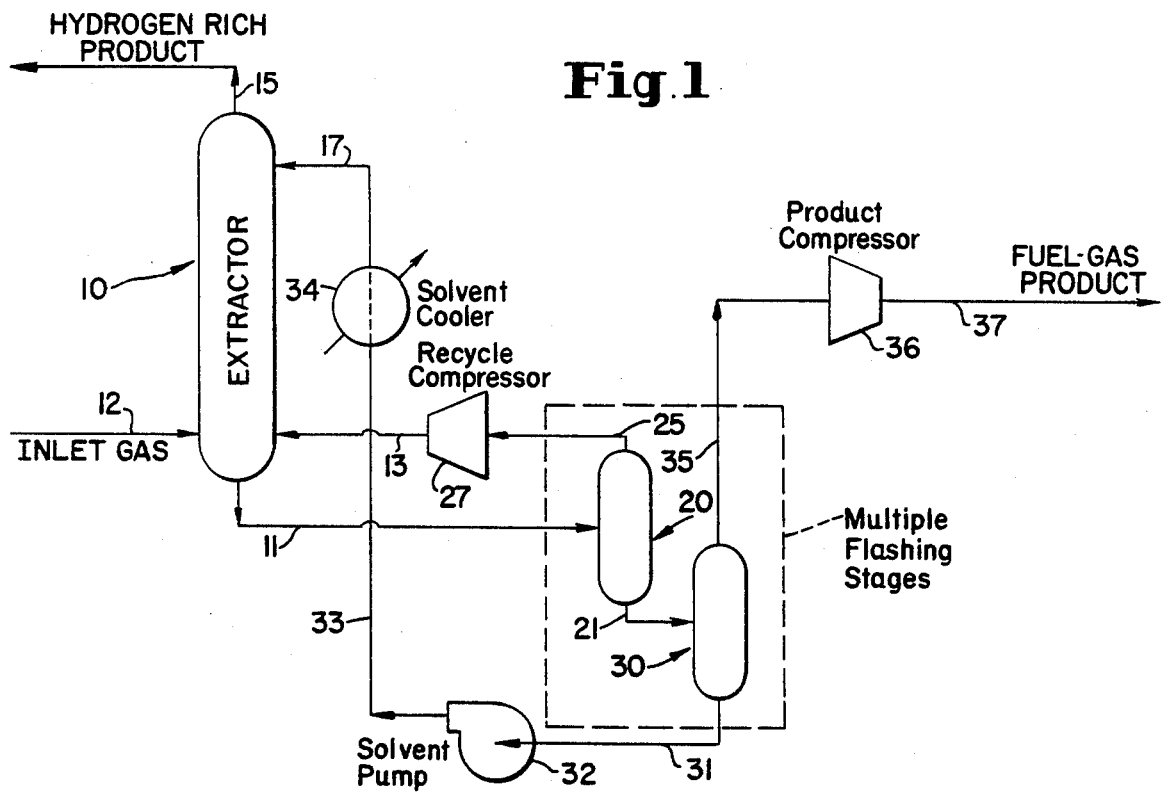
FIG. 1 is a schematic flow sheet for extractive flashing in two stages without distillative regeneration of the solvent.

FIG. 1 illustrates use of the Mehra Process for recovery and economical purification of approximately 90% to 95% of contained hydrogen from refinery and petrochemical off-gas streams. This embodiment of the process uses combinations of extracting and flashing steps. Inlet stream 12 of hydrogen-containing gas is contacted within extractor column 10 with the lean solvent in stream 17. Gas stream 12 enters extractor column 10 near its bottom and flows upward where it contacts the lean solvent from entering stream 17 which flows downward in a countercurrent manner. The contact takes place over mass transfer surfaces.

The hydrogen-rich gas product leaves column 10 as overhead stream 15 from the top of column 10. The rich solvent carrying the undesirable components leaves the bottom of extractor column 10 as stream 11 and is let down in pressure in a single stage if (1) inlet stream 12 is essentially a mixture of hydrogen and methane or at least contains no compound boiling significantly higher than the boiling point of methane, and (2) the desired hydrogen recovery is relatively modest (not greater than approximately 95%). However, multiple flashing stages 20, 30, as shown in FIG. 1, may be needed to separate the extracted hydrocarbons from the solvent, if $C_2+$ hydrocarbons are present in the inlet off-gas stream.

Some of the desirable hydrogen is dissolved in rich solvent stream 11. The desirable hydrogen is then preferentially separated from the solvent in the initial flashing stage or stages (e.g., stage 20) by selecting the flashing pressure or pressures and is then recycled to the extractor column as stream 25. Alternatively, these gases can flow directly to fuel gas product stream 37.

When there are two stages, for example, as shown in FIG. 1, the flashed-off gases leave stage 20 in overhead stream 25, are compressed to the pressure of the inlet gas in stream 12 by recycle compressor 27, and are then recycled as stream 13 to column 10.

Bottoms from stage 20 flow as stream 21 to the next lower-pressure flashing stage, such as stage 30, which is at a selected lower pressure. Flashed-off gases are separated from solvent therewithin.

The final pressure to which the rich solvent is flashed depends upon the compounds that are present in the rich solvent. Considering saturated hydrocarbons only, as an example, if methane is the only hydrocarbon in a hydrogen-containing gaseous mixture being extracted, 150 psig is satisfactory. If ethane is the highest molecular-weight hydrocarbon in the mixture, the pressure must be lower and if propane, still lower. However, if butanes and/or heavier hydrocarbons are present, the final stage must be at vacuum, such as 2 psia.

The number of stages is a function of both the required recovery of hydrogen and the required pressure drop which depends upon both the inlet pressure and the pressure of high molecular-weight compounds. For example, if the pressure drop is large, such as 800 psi, 4-6 stages may be used, but if it is relatively small, such as 225 psi, two stages are satisfactory. In general, multiple stages (i.e., at least two) are generally economical if recovery of hydrogen must be greater than 90%.

If high molecular-weight compounds, such as lube oil, are present in trace quantities, a front-end carbon filter should be used to prevent build-up thereof in the solvent. If $C_{4+}$ hydrocarbons are present in significant quantities, a front-end cooler and a separator are advisable.

The separated solvent in stream 31 from the last flashing stage (e.g., stage 30) is pumped by solvent pump 32 through line 33 and cooled in solvent cooler 34 before being recycled to extractor column 10 as stream 17 for further extraction of undesirable hydrocarbons. Depending upon the selected temperature of the solvent, the cooling may be accomplished by cooling water or appropriate refrigeration. The undesirable hydrocarbons separated in the latter flashing stages, such as in stream 35, may be compressed by product compressor 36 and cooled, if desired, to leave the process unit as fuel gas product in stream 37.

EXAMPLE 1

The capital and operating requirements of a plant designed with this process configuration, to recover 94% of contained hydrogen from a catalytic reformer tail gas stream to produce 95 mol % purity hydrogen product, are outlined in Table II.

TABLE II

| Off-gas | | |
|---|---|---|
| Flow rate | 15.0 MMSCFD | |
| H$_2$ Purity | 80 mol % | |
| Pressure | 150 psig | |
| Hydrogen Product | | |
| Flow rate | 11.9 MMSCFD | |
| Purity | 95 mol % | |
| Pressure | 1290 psig | (Note 1) |
| Recovery | 94% | |
| Fuel Gas Product | | |
| Flow rate | 2.4 MMSCFD | |
| Pressure | 50 psig | |
| Gross heating value | 1025 Btu/SCF | |
| LPG Product | | |
| Flow rate | 503 BPSD | |
| Pressure | 310 psig | |
| Capital Investment | $3.0 MM | |
| (March 1987 basis) | | |
| Fuel Requirements | 0.56 MMBTU/HR | (Note 2) |
| Electricity | 947 KW | |
| Solvent Loss | $400/Year | (Note 3) |

Note 1 Catalytic reformer tail gas compression exists.
Note 2 Primarily in the form of 50 psig saturated stream.
Note 3 Excludes leaks & miscellaneous losses.

When the hydrogen-rich gas stream contains significant amounts of hydrocarbons heavier than methane, it may be economically desirable to process such an inlet gas stream for recovering:
(a) a hydrogen product of specified purity;
(b) a methane-rich fuel gas product; and
(c) an ethane and heavier hydrocarbons liquid product, measured as barrels per stream day (BPSD).

Figure 2:
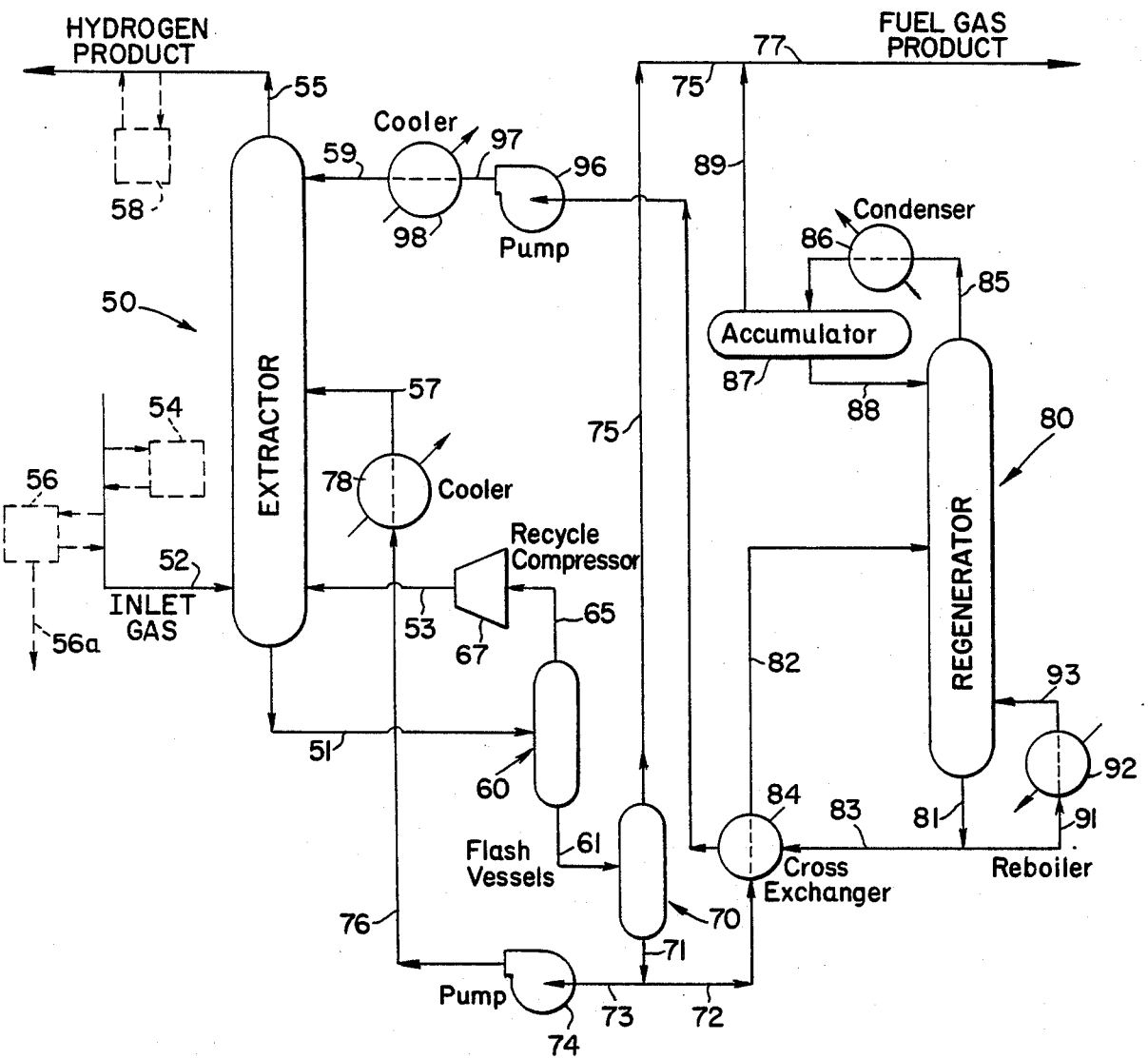
FIG. 2 is a schematic flow sheet for extractive flashing in two stages and slipstream regeneration of the solvent.

A combination of extractive-flashing and slipstream regenerating operations of selected magnitude is shown in FIG. 2 for recovering high-purity hydrogen under high recovery levels according to the Mehra Process.

Inlet stream 52 is extracted in an extractor column 50 with the lean physical solvent. The rich solvent in bottoms stream 51 is flashed in at least one flashing stage. A single stage is sufficient if the desired hydrogen recovery is relatively modest and if $C_{2+}$ hydrocarbons are not present in inlet stream 52. When multiple flashing stages 60, 70 are needed within at least two flashing vessels, as shown in FIG. 2, the gases leaving the first stage as overhead stream 65 are compressed by recycle compressor 67 and recycled as stream 53 to extractor column 50 since they contain mostly dissolved hydrogen.

The partially stripped solvent leaving the bottom of stage 60 as stream 61 flows to stage 70. The gases leaving at least the last flashing stage 70 as stream 75 primarily consist of methane and other hydrocarbons which are present in inlet off-gas stream 52 and become part of the fuel gas product in stream 77.

The solvent leaving the bottom of the second flashing stage 70 as stream 71 is split into two streams, major and minor. The major portion of the solvent stream in line 73 is pumped by pump 74 through line 76 and cooler 78 to extractor column 50 as solvent stream 57. The minor portion is a slipstream 72 which is heated in cross exchanger 84 and then fed as stream 82 to solvent regenerator 80, wherein all contained extracted components are separated from the solvent which is thereby regenerated.

The overhead gases in stream 85 are cooled in condenser 86, separated in accumulator 87 from higher-boiling components, and fed as stream 89 to join the gases from the last flashing vessel 70 and form the fuel gas product in stream 77. The higher-boiling components are returned as reflux stream 88 to the top of the regenerator column.

The regenerated lean solvent in line 81 is split into a reboiler stream 91 and recycle stream 83 which is cooled in cross exchanger 84, pumped throuqh lines 95 and 97 by pump 96 and further cooled in cooler 98 before being fed to the top of column 50 as very lean solvent stream 59. Reboiler stream 91 is heated in reboiler 92 and recycled to the lower part of the regenerator column as stream 93.

EXAMPLE 2

The capital and operating requirements of a plant designed to upgrade catalytic reformer tail gas to recover 95% of contained hydrogen as 97 mol % purity hydrogen product are given in Table III.

TABLE III

| Off-gas | | |
|---|---|---|
| Flow rate | 15 MMSCFD | |
| H$_2$ Purity | 80 mol % | |
| Pressure | 150 psig | |
| Hydrogen Product | | |
| Flow rate | 11.8 MMSCFD | |
| Purity | 97 mol % | |
| Pressure | 1290 psig | (Note 1) |
| Recovery | 95% | |
| Fuel Gas Product | | |
| Flow rate | 2.5 MMSCFD | |
| Pressure | 50 psig | |
| Gross heating value | 1085 Btu/SCF | |
| LPG Product | | |
| Flow rate | 503 BPSD | |
| Pressure | 310 psig | |
| Capital Investment | $3.5 MM | |
| Fuel Requirements | 3.29 MMBTU/HR | (Note 2) |
| Electricity | 169 KW | |
| Solvent Loss | $10,800/Year | (Note 3) |

Note 1 March 1987 basis - Catalytic reformer tail gas
Note 2 Includes 465 lbs/hr of 50 psig saturated stream
Note 3 Excludes leaks & miscellaneous loss.

Both process embodiments are quite flexible in recovering only the selected components and are shown in FIGS. 1 and 2 merely as two portions of a spectrum of process possibilities from zero regeneration for no inlet $C_{4+}$ hydrocarbons to selective regeneration when required.

Such flexibility is achieved by selecting the temperature and flow rate of the lean solvent stream or streams with respect to composition and flow rate of the inlet gas stream, flashing pressures, quantity of the slipstream, use of an activated carbon bed, and use of a front-end cooling unit. Should the economic conditions change, the process is capable of producing alternate purity hydrogen product.

This operational flexibility can be achieved by changing the operating conditions on-line as to the quantity of the slipstream from zero as shown in FIG. 1 to any amount up to 40% as shown in FIG. 2, temperatures at the bottom of the extractor column, number of flashing stages, number of overhead flash streams that are recycled to the extractor column, and temperatures of the cooled solvent streams. There is no need to change the solvent before switching the operation.

Additional flexibility is achieved by selecting the flashing pressure for one or more of the successive flashing stages, thereby selectively recycling the more desirable flashed gas streams to the extraction column.

Since the hydrogen pressure requirements vary from 150 to 3000 psia, depending upon the application from catalytic reforming to hydrotreating to desulfurization to resid hydrocracking, for example, it is preferred to process the inlet gas stream at the highest available pressure, since the recovered hydrogen must be compressed to user pressure. This is economical because the Mehra Process unit delivers the hydrogen essentially at the same pressure as the inlet pressure to the plant. However, delivery pressures between 200 and 1400 psia are more than adequate. Depending upon the selected configuration of this invention process and use of a reboiler at the bottom of the extraction column, the operating temperatures of the extraction column can vary between 300° F. and −40° F. These conditions allow the Mehra Process plant to meet the desired objectives of recovery and purity with low solvent circulation rates.

This process effectively utilizes blends of $C_8$ to $C_{10}$ aromatic compounds having methyl, ethyl, propyl, or butyl aliphatic groups, specifically constituting a subgroup of mesitylene, n-propyl benzene, n-butyl benzene, cumene, o-, m-, and p-xylenes, and other $C_8$14 $C_{10}$ aromatics. Additional solvents that are useful include specially blended mixtures of dialkyl ethers of polyalkylene glycol, n-methyl pyrrolidone, dimethyl formamide, propylene carbonate, sulfolane, and glycol triacetate.

The preferred physical solvents possess high component selectivities and high hydrocarbon loading capacities. The selected preferred solvents are also non-foaming, non-degrading, and non-corrosive. The selected solvents do not require any catalysts, chemicals, or inhibitors and can process sweet or sour gas streams.

Since this is a solvent-based process, it is important that the solvent losses be minimized. Since the selected solvent has a low vapor pressure and a low freezing point, appropriate selection of operating conditions minimizes the solvent losses. However, if presence of trace solvent in the hydrogen-rich product is detrimental to downstream processing, such solvent traces can be conveniently removed from the hydrogen product by passing recovered gas streams 15, 55 through an activated carbon filter 58.

It is also important to maintain the effectiveness of the preferential physical solvent by preventing any build-up of compressor oils or other heavier hydrocarbons present in the inlet gas streams. These contaminants have molecular weights which are higher than those of the selected solvent. Since the process does not require desiccant bed dehydration which is necessary for cryogenic processing, any traces of glycol present in the gas streams from glycol dehydration systems also tend to accumulate in the solvent. Such traces of glycol, compressor lube oils, and other heavier hydrocarbons are easily removed from inlet gas streams 12, 52 by installing an activated carbon bed filter 54 upstream of extraction column 50, for example. A solvent reclaimer may also be economically utilized on streams 31 and 83.

When heavier hydrocarbons are present in significant quantities, the inlet gas is cooled to a temperature at which these hydrocarbons are selectively condensed in front-end cooler 56 and are then separated from the gas stream before the extraction step. The separated hydrocarbons are stabilized and bypass the main plant as stream 56a. This step prevents contact of such heavier components with the solvent, thereby ensuring ongoing benefits of solvent selectivity and operational flexibility as well as reducing energy requirements and solvent quantities related to solvent regeneration.

As has been shown, the Mehra Process technology offers a new and unique alternative for the purification and recovery of hydrogen from various refinery and petrochemical off-gas streams. As with other technologies, it is important to identify and quantify trace components as well as to define the desired objectives of purity and recovery levels of hydrogen gas product. To meet the challenge created by the need to increase hydrogen supplies, off-gas streams can be economically processed via this non-cryogenic solvent extraction process to produce high pressure hydrogen gas product under high purity and recovery levels.

Because it will be readily apparent to those skilled in the art of treating hydrocarbon gases and hydrogen off-gases that innumerable variations, modifications, applications, and extensions of the examples and principles hereinbefore set forth can be made without departing from the spirit and the scope of the invention, what is hereby defined as such scope and is desired to be protected should be measured, and the invention should be limited, only by the following claims.

What is claimed is:

1. A process for producing a hydrogen-rich gas product stream as an overhead stream and a rich solvent stream as a bottoms stream from an inlet stream of gas comprising hydrogen and hydrocarbons by contacting said inlet hydrogen-containing gas stream with a stream of lean preferential physical solvent in which said hydrocarbons are more soluble and less volatile than hydrogen, said solvent being:

A. selected from the group consisting of dialkyl ethers of polyalkylene glycol, N-methyl pyrrolidone, dimethylformamide, propylene carbonate, sulfolane, glycol triacetate, and $C_8$ to $C_{10}$ aromatic compounds having methyl, ethyl, propyl, or butyl aliphatic groups specifically constituting a sub-group of mesitylene, n-propyl benzene, n-butyl benzene, cumene, o-xylene m-xylene, p-xylene and mixtures thereof and aromatic streams rich in mixed xylenes; and other $C_8$–$C_{10}$ aromatics; and B. selective for methane and heavier hydrocarbon components of said inlet gas stream such that:
  (1) the relative volatility of hydrogen over methane is at least 4.5 and the hydrocarbon loading capaicty, defined as solubility of methane in said solvent, is at least 1.0 standard cubic feet of methane to a gallon of said solvent, or
  (2) the preferential factor, determined by the multiplication of relative volatility of hydrogen over methane by the solubility of methane in solvent, in standard cubic feet of methane per gallon of solvent stream are least 4.5, said contacting being conducted within at least one column to which said inlet gas stream and said lean solvent stream are fed, whereby said inlet gas stream and said solvent stream pass countercurrently therewithin to produce said overhead stream and said bottoms stream.

2. The process of claim 1, wherein said solvent selectively extracts said hydrocarbons from said inlet gas stream to provide selective capability for recovery of:
A. hydrogen having a purity of 90% to 99% as said overhead stream; and
B. most of said methane and substantially all of said materials more soluble than said methane that are in said solvent, as said fuel gas streams.

3. The process of claim 1, wherein said inlet gas stream is selected from the group consisting of thermally cracked hydrocarbon gas, catalytically cracked hydrocarbon gas, refinery off-gas, coke-oven gas, synthesis gas, refinery HT purge gas, refinery FCC gas, refinery cascade reject gas, methanol purge gas, ethylene byproduct hydrogen, ethylene cracked gas, LPG dehydrogenation product gas, toluene HDA hydrogen purge gas, cyclohexane hydrogen purge gas, carbon black product gas, formaldehyde byproduct hydrogen, and ammonia purge gas.

4. The process of claim 3, wherein said hydrocarbons principally comprise methane.

5. The process of claim 4, wherein said hydrocarbons additionally comprise olefins and hydrocarbons heavier than methane.

6. The process of claim 5, wherein said hydrocarbons heavier than methane comprise ethane, propane, and/or butane, and said olefins comprise ethylene, propylene, butene, and diolefins.

7. A process for producing a hydrogen-rich gas procuct stream as an overhead stream and a rich solvent stream as a bottoms stream from an inlet stream of gas comprising hydrogen and hydrocarbons by contacting said inlet hydrogen-containing gas stream with a stream of lean preferential physical solvent in which said hydrocarbons are more soluble and less volatile than hydrogen, said contacting being conducted within at least one column to which said inlet gas stream and said lean solvent stream are fed, whereby said inlet gas stream and said solvent stream pass countercurrently therewithin to produce said overhead stream and said bottoms stream, wherein:

A. said bottoms stream is successively flashed at least twice to produce:
  (1) a fuel gas product stream comprising at least most of said hydrocarbons, and
  (2) a lean solvent stream which is recycled to said at least one column;
B. the overhead stream from at least the first of said successive flashing stages is recycled to said column, the overhead streams from the remaining flashing stages being combined to form said fuel gas product stream; and
C. the bottoms stream from the last of said successive flashing stages is divided into major and minor portions, said major portion being recycled to said column for feeding approximately to the mid point thereof and said minor portion being fed as a slipstream to a distillation column for regenerating to form a very lean solvent stream for recycling to said column and feeding to the top thereof, whereby two stages of extracting occur within said column and said overhead stream is substantially purer than 95% purity hydrogen.

8. A process for separating hydrogen and $C_1+$ hydrocarbons from a hydrogen-containing inlet gas stream which comprises more than 5 mol % of said hydrogen, said process comprising the following steps:
A. extracting said inlet gas stream with a preferential physical solvent to produce an overhead stream which is at least hydrogen-rich and a bottoms stream which is hydrocarbon-rich solvent,
B. flashing said bottoms stream at a flashing pressure which is selected to be between 800 psia and 2 psia and is sufficiently low that substantially all said $C_1+$ hydrocarbons are separated from a stripped solvent stream and are produced as a stream of flashed-off gases, and
C. recycling said stripped solvent stream to said extracting of said Step A,
wherein:
  1. said inlet gas stream is extracted in two stages with said physical solvent to remove said substantially all of said methane and substantially all of materials in said gas stream which are more soluble than said methane in said solvent, whereby said overhead stream from said extracting is at least 95% hydrogen;
  2. said inlet gas stream is extracted in the first stage of said two stages with a major part of said solvent stream containing less than 10 wgt. % of hydrocarbons to produce a partially stripped gas stream, and
  3. said partially stripped gas stream is extracted in the second stage of said two stages with a very lean solvent stream to produce said pure hydrogen stream and an enriched solvent stream.

9. The process of claim 8, wherein said flashing step utilizes up to eight flashing stages, having a ratio of absolute pressures between successive said flashing stages of at least 2.0.

10. The process of claim 8, wherein said enriched solvent stream is added to said major solvent stream in said first stage of said two stages for extracting said inlet gas stream, whereby said rich solvent stream is produced.

* * * * *

UNITED STATES PATENT AND TRADEMARK OFFICE
CERTIFICATE OF CORRECTION

PATENT NO. : 4,740,222        Page 1 of 2
DATED      : April 26, 1988
INVENTOR(S): Yuv R. Mehra It is certified that error appears in the above-identified patent and that said Letters Patent is hereby corrected as shown below:

Title page, designation [75], change "Yuy" to --Yuv--.

Column 2, line 40, change "$CO_2$" to --$CO_2$--.

Column 2, line 40, change "$O_2$" to --$O_2$--.

Column 2, line 40, change "$H_2O$" to --$H_2O$--.

Column 3, line 37, change "$CO+H_2O \rightarrow CO_2+H_2$" to --$CO+H2O \rightarrow CO2+H2$--.

Column 3, line 61, change "$CO+3H_2 \rightarrow CH_4+H_2O$" to --$CO+3H2 \rightarrow CH4+H2O$--.

Column 11, line 50, change "$C_814C_{10}$" to --$C_8-C_{10}$--.

Claim 1, column 12, line 68, change "o-xylene m-xylene" to --o-xylene, m-xylene--.

Claim 1, column 13, line 6, change "capaicty" to --capacity--.

UNITED STATES PATENT AND TRADEMARK OFFICE
CERTIFICATE OF CORRECTION

PATENT NO. : 4,740,222

DATED : April 26, 1988

INVENTOR(S) : Yuv R. Mehra

It is certified that error appears in the above-identified patent and that said Letters Patent is hereby corrected as shown below:

Claim 1, column 13, lines 15 and 16, change "solvent stream are least 4.5" to --solvent, is at least 4.5--.

Claim 7, column 13, lines 51 and 52, change "pro-cuct" to --pro-duct--.

Signed and Sealed this

Twentieth Day of September, 1988

Attest:

DONALD J. QUIGG

Attesting Officer

Commissioner of Patents and Trademarks